(12) United States Patent
Kartmann et al.

(10) Patent No.: US 12,380,993 B2
(45) Date of Patent: Aug. 5, 2025

(54) METHOD AND SYSTEM FOR IMAGE-BASED OPERATIONAL DECISION SUPPORT

(71) Applicant: Siemens Healthcare GmbH, Erlangen (DE)

(72) Inventors: René Kartmann, Nuremberg (DE); Benedikt Krüger, Ebensfeld (DE); Peter Gall, Uttenreuth (DE); Lars Lauer, Neunkirchen (DE); Jens Gühring, Erlangen (DE)

(73) Assignee: Siemens Healthineers AG, Erlangen (DE)

( * ) Notice: Subject to any disclaimer, the term of this patent is extended or adjusted under 35 U.S.C. 154(b) by 435 days.

(21) Appl. No.: 17/939,163

(22) Filed: Sep. 7, 2022

(65) Prior Publication Data

US 2023/0070444 A1  Mar. 9, 2023

(30) Foreign Application Priority Data

Sep. 7, 2021 (EP) .................................... 21195358

(51) Int. Cl.
*G16H 30/40* (2018.01)
*G06T 7/00* (2017.01)
(Continued)

(52) U.S. Cl.
CPC ............. *G16H 30/40* (2018.01); *G16H 30/20* (2018.01); *G06T 7/0012* (2013.01); *G06T 2207/20081* (2013.01); *G16H 50/20* (2018.01)

(58) Field of Classification Search
CPC ........ G16H 30/40; G16H 30/20; G16H 50/20; G16H 40/63; G06T 7/0012;
(Continued)

(56) References Cited

U.S. PATENT DOCUMENTS 6,574,304 B1   6/2003 Hsieh et al.
2004/0064037 A1*  4/2004 Smith ................... G06T 7/0012
                                                      600/420
(Continued)

FOREIGN PATENT DOCUMENTS

EP     3599611 A1    1/2020
EP     3637424 A1    4/2020
(Continued)

OTHER PUBLICATIONS

"Clinical Practice Guidelines", National Center for complementary and Integrative Health, https://www.nccih.nih.gov/health/providers/clinicalpractice.

*Primary Examiner* — Santiago Garcia
(74) *Attorney, Agent, or Firm* — Banner & Witcoff Ltd.

(57) ABSTRACT

Techniques are described for providing image-based operational decision support. The technique includes providing initial imaging data from a preceding examination of a patient, determining clinical findings by automated processing of the initial imaging data, generating decision data at least comprising a decision whether a further recording of a number of images is necessary, and generating a suggested set of imaging parameter values for recording this number of images. The decision data may be based on the determined clinical findings, and the technique may further include outputting the suggested set of imaging parameter values for recording a number of images of the patient. Also described are a related clinical decision system, a decision module, and a related medical imaging system.

20 Claims, 2 Drawing Sheets

(51) Int. Cl.
*G16H 30/20* (2018.01)
*G16H 50/20* (2018.01)

(58) Field of Classification Search
CPC . G06T 2207/20081; G06T 2207/20084; G06T 2207/30096; G06N 3/0464; G06N 3/096; G06N 3/045; G06N 3/09
See application file for complete search history.

(56) References Cited

U.S. PATENT DOCUMENTS

| | | | |
|---|---|---|---|
| 2005/0049497 A1 | 3/2005 | Krishnan et al. | |
| 2008/0052112 A1* | 2/2008 | Zahlmann | G16H 10/20 |
| | | | 705/2 |
| 2010/0086189 A1 | 4/2010 | Wang et al. | |
| 2017/0069081 A1* | 3/2017 | Gluncic | G16H 30/40 |
| 2018/0144465 A1* | 5/2018 | Hsieh | G06N 3/04 |
| 2018/0253842 A1* | 9/2018 | Allmendinger | G06V 10/87 |
| 2018/0344284 A1* | 12/2018 | Freudenberger | G06N 3/045 |
| 2019/0053876 A1* | 2/2019 | Sterental | B29C 64/386 |
| 2019/0156477 A1* | 5/2019 | Perrin | G06T 7/0012 |
| 2019/0228857 A1 | 7/2019 | Lin et al. | |
| 2019/0304093 A1* | 10/2019 | Duval | G16H 30/40 |
| 2020/0365267 A1 | 11/2020 | Lauer | |
| 2020/0402236 A1* | 12/2020 | Courot | G16H 15/00 |
| 2021/0075770 A1 | 3/2021 | Brost | |
| 2021/0118554 A1 | 4/2021 | Amthor et al. | |
| 2021/0327055 A1* | 10/2021 | Putha | G06V 10/774 |
| 2021/0407694 A1 | 12/2021 | Deckert et al. | |
| 2023/0072095 A1 | 3/2023 | Krüger et al. | |

FOREIGN PATENT DOCUMENTS

| | | |
|---|---|---|
| EP | 3758015 A1 | 12/2020 |
| EP | 3837693 A1 | 6/2021 |
| WO | 2009050676 A1 | 4/2009 |

* cited by examiner

METHOD AND SYSTEM FOR IMAGE-BASED OPERATIONAL DECISION SUPPORT

CROSS-REFERENCE TO RELATED APPLICATIONS

The present application claims the benefit of the filing date of Europe patent application no. EP 21195358.3, filed on Sep. 7, 2021, the contents of which are incorporated herein by reference in their entirety.

TECHNICAL FIELD

The disclosure is directed to techniques for image-based operational decision support. In particular, the disclosure describes a method and a device for controlling a medical imaging system, e.g. a magnetic resonance imaging system or a computed tomography system. The disclosure provides a test algorithm chain in imaging, which may be based on deep learning.

BACKGROUND

In medicine, there is often a sequence of diagnostic steps for certain medical conditions, e.g. illnesses. Regarding an examination to be performed, this examination may strongly depend on a finding or a result of a previous imaging diagnosis. For example, a diagnostic mammography is only carried out after a mammography screening with a suspicious finding or a chest CT is performed after an X-ray examination of the chest with a suspicious finding.

Especially in medical imaging, often a sequence of medical imaging scans can be necessary to accurately diagnose a certain medical condition of a patient. In the sequence of medical imaging scans, typically the performance of a certain kind of medical imaging scan is based on the results of a previously-performed medical imaging scan.

For example, an MRI scan of the abdomen region may lead to incidental findings of suspicious lesions in the liver of the patient, which leads to the necessity of a follow-up MRI scan focused on the liver of the patient, potentially employing special MRI techniques to be able to generate liver images (e.g. DIXON-imaging, zoomed imaging, special motion compensation techniques, etc.). As a further example, the results of the MRI scan might turn out to be insufficient to diagnose a certain condition of the patient, so that the MRI scan needs to be repeated with different imaging conditions, e.g. employing different kind of MRI imaging sequences or the injection of a contrast agent.

SUMMARY

Up to now, there is the possibility to aid examinations with an automated diagnosis.

For instance, U.S. Pat. No. 6,574,304 B1 describes processing first imaging data from a first imaging system with a computer-aided diagnosis (CAD) algorithm and acquiring second imaging data based upon the results of the CAD algorithm to enable a complete useful set of information to be gathered during a single patient session. The subsequent acquisition may include acquisition of data from other regions of the patient's body, at different orientations with respect to tissues of interest, at different resolution levels, and so forth.

Typically, images produced in a first medical imaging scan have to be assessed, e.g. by a radiologist, to prescribe the follow-up scan of the patient. This might lead to several disadvantages:

A time delay between the first medical imaging scan and the follow-up scan leading to a delay in providing the correct diagnosis of the patient and a delay in the start of the treatment;

organizational burden and further costs as a follow-up scan of the patient needs to be scheduled and performed (including the necessity to perform again a time-consuming preparation of the patient for the follow-up scan); and patient dissatisfaction.

Conventionally, the clinical context of the patient is not taken into account, but only the patient imaging data. Therefore, known procedures and systems do not leverage the full information available for a certain patient.

It is thus the object of the present disclosure to improve the known systems, devices, and methods to facilitate an improvement in image-based operational decision support, especially in controlling a medical imaging system.

This object is achieved by the embodiments described herein, including the claims.

The present disclosure describes an implementation of a "test-algorithm chain in medical imaging" with a particular focus on a specific implementation for magnetic resonance imaging (MRI). Of course, the described framework may also be applied in other forms of diagnostic imaging, e.g. computed tomography (CT), X-ray imaging, positron emission tomography (PET), single-photon emission computed tomography (SPECT), ultrasound, molecular imaging, or other suitable medical imaging procedures.

A method according to the disclosure for image-based operational decision support comprises the following steps:
  providing initial imaging data from a preceding examination of a patient;
  determining clinical findings by automated processing of the initial imaging data (e.g. by computer aided diagnosis);
  generating decision data at least comprising a decision whether a further recording of a number of images is necessary and generating a suggested set of imaging parameter values for recording this number of images, wherein the decision data is based on the determined clinical findings; and
  outputting the suggested set of imaging parameter values for recording a number of images of the patient.

A decision module according to the disclosure for performing a method according to the disclosure is designed to generate, based on clinical findings in initial imaging data of a patient, decision data indicating whether a number of additional medical images should be recorded. The decision module is further designed to generate a suggested set of imaging parameter values designed to control an imaging modality for recording this number of additional medical images.

A clinical decision system according to the disclosure is provided for image-based operational decision support, e.g. for performing the method according to the disclosure, and comprises the following components:
  a data interface designed for receiving initial imaging data from a preceding examination of a patient;
  a CAD engine designed for determining clinical findings by automated processing of the initial imaging data (e.g. by computer aided diagnosis);
  a decision module according to the disclosure; and a data interface designed for outputting the suggested set of imaging parameter values for recording a number of images of the patient.

The general idea is to use results of a tool like the AI Rad Companion to (automatically) order a further exam. Clinical decision support systems guiding the scan or examination workflow while the patient is still positioned in the scanner, or at least shortly after the patient leaves the scanner, can lead to very efficient and result-oriented scanning also in the diagnostic imaging arena. The underlying general workflow would be that the AI-Rad Companion or a similar tool receives an imaging exam result (of whatever modality, e.g. a DICOM image), recommends what to do next, and basically enables a so called "test-algorithm chain" in imaging. The output of data (suggested set of imaging parameter values or possibly additional data) serves the acquisition of additional images and, thus, the control of a medical imaging system.

The specific problem that is addressed by this disclosure is to provide a test algorithm chain automatically providing a possible solution space for a further step after a certain initial finding, in addition with suitable parameter values for image recording. The general structure as described herein forms the basis for above method and clinical decision system.

At first, a patient undergoes a first medical imaging examination. This examination could e.g. be a computed tomography (CT), a magnetic resonance imaging (MRI), an X-ray imaging, positron emission tomography (PET), single-photon emission computed tomography (SPECT), ultrasound, etc., related to a specific medical question.

Suitable imaging data for the disclosure may include any suitable types of digital medical images, e.g. X-ray images, CT-images, or MR-images. Regarding the images, it could be advantageous to imagine a preferred case in which the images are scans of a patient and the parameters are scan parameters.

The initial imaging data is e.g. a number of digital images from a preceding scan of a patient. This initial imaging data may be retrieved from a database. However, it could be advantageous to apply the method at the time of the examination. Then, the step of providing initial imaging data may be split into the following sub-sets:

providing an initial set of imaging parameter values, e.g. by a semi-automatic or an automatic process;

recording an image based on the initial set of imaging parameter values, wherein the resulting initial imaging data is provided for the determination of findings and e.g. also for the generation of the set of imaging parameter values.

The initial set of imaging parameter values can be set by known manual processes, e.g. by using a control console of a medical imaging system, semi-automatic processes, or automatic processes, e.g. using machine learning algorithms, which take MRI localizer images as an input and output the initial set of imaging parameter values. In some embodiments, the initial set of imaging parameter values can form a complete set of values for all imaging parameters needed for performing a first scan with a medical imaging system. Therefore, the initial set of imaging parameter values may be adapted for generation of medical images suitable for assessing the specific medical condition, which the prescription for the first scan with the medical imaging system is based on.

The initial set of imaging parameter values is then used for the first scan with the medical imaging system. In addition, the initial set of imaging parameter values can optionally be used as an input for the decision engine and/or the parameter setting engine.

Based on the received initial set of imaging parameter values, a first scan of the patient is performed, with the medical imaging system producing the initial medical imaging data. The initial medical imaging data should be suitable for assessing the specific medical condition, which the prescription for the first scan with the medical imaging system is based.

After the initial imaging data is provided, the resulting initial imaging data from the first examination is provided to an image processing system, e.g. based on machine learning (ML) and/or on artificial intelligence (AI), e.g. the AI-Rad Companion. This (AI/ML-based image processing system is designated herein with the expression "CAD engine" (CAD: "computer aided diagnostics") and may be located on premises or outside of the hospital, e.g. as part of a cloud computing system. The initial imaging data is received by a data interface and provided for the methods described herein.

The CAD engine receives the initial medical imaging data, processes them, and generates clinical findings based on the initial medical imaging data. The clinical findings are later used as an input for the decision engine. Additionally, the clinical findings can optionally be used as an input for the parameter setting engine.

The clinical finding can be a diagnosis, a structured report, another image (e.g. a segmentation of the input image), etc. Additionally or alternatively, the clinical findings can comprise a measure for the quality or the reliability of the diagnosis (e.g. a number between 0 and 1 indicating how sure a certain finding is). It is preferred that a user has a manual possibility to verify the clinical findings. This has the advantage that possible errors due to automatic processing can be reduced.

In an embodiment, the CAD engine includes an automatic processing algorithm that receives the initial medical imaging data as input data and generates the clinical findings as output data. Such CAD engines are well known in the art. An example CAD engine for this purpose may include appropriate pre-processing algorithms applied on the initial medical imaging data (e.g. segmentation, landmark detection, registration, etc.). Another example CAD engine comprises the usage of a reference atlas to process the initial medical imaging data (e.g. in case of brain MRI input data) to generate the clinical findings. Another example CAD engine comprises one or more suitable (deep) neural network(s), e.g. convolutional neural network(s), applied on the initial medical imaging data as input data to generate the clinic al findings.

Clinical findings generated by the CAD engine may comprise one item or a combination of the items, examples of which are provided in the following list:

a binary indication of whether the patient is afflicted with a certain medical condition or not;

an indication with which medical condition(s) the patient is afflicted (including incidental findings not connected to specific medical condition to be assessed by the CAD engine);

a probability (e.g. percentage value or other suitable indication that the patient is afflicted with a certain medical condition);

a (e.g. numerical) indication about the severity of the affliction of the patient with a certain medical condition, an indication regarding the stage/staging of a certain disease which the patient is afflicted; and spatially-resolved localization data.

The spatially-resolved localization data may be e.g. saved in any suitable data format, e.g. the DICOM format, and may include e.g. one or more of the following information:

- a spatial distribution of the (severity of the) affliction of the patient with a certain medical condition;
- the position(s) of suspicious finding(s) (e.g. lesion, nodule, abnormality) in the initial medical imaging data;
- a segmentation of the initial medical imaging data. Such segmentation may e.g. include a segmented region in the initial medical imaging data, being an area containing features indicating the affliction of the patient with a certain medical condition;
- certain (sets of) coordinates in the initial medical imaging data;
- a segmentation map having the same or a lower resolution than the first medical imaging data; and
- spatially-resolved numerical values in the same or a lower resolution than the initial medical imaging data.

Based on the findings, the decision data and the suggested set of imaging parameter values are generated. The expression "suggested" means that the set of imaging parameter values is generated automatically, and may be controlled by a user before applying it to an imaging process. The decision data can be generated by a decision engine and the suggested set of imaging parameter values by a parameter setting engine, wherein both engines may also be formed by one combined engine. It should be noted that the suggested set of imaging parameter values is only generated in the case in which an image should be recorded in a following exam. Thus, the generation of the suggested set of imaging parameter values should also depend on decision data. However, in such a case, a specially-trained decision module may be used, and the suggested set of imaging parameter values could also be directly generated from the clinical findings represent the decision data, wherein their presence itself indicates a decision for a following image recording.

The clinical findings are used as input to the decision engine that can also comprise an AI/ML algorithm. The decision engine can be part of the same system as the CAD engine, or both can be related to different systems. The decision engine can be an offering on-premises or a cloud-based computing system.

The decision engine takes the clinical findings generated by the above described CAD engine as inputs, processes them, and presents a decision as output to the parameter setting engine (decision data). Generally, the decision engine is designed to generate a decision regarding whether a further recording of a number of images, e.g. a follow-up scan, is needed or is advantageous based on the clinical findings. Furthermore, the decision engine may be designed to generate a decision based on the clinical findings regarding what kind of diagnostic goal should be pursued by the follow-up scan, i.e. which medical condition, which is suspected based on the clinical findings, should be the target of the follow-up scan.

In case the input data (i.e. the clinical findings and maybe further data) comprise a binary indication whether the patient is afflicted with a certain medical condition or not, the decision engine can work with existing lookup tables to determine if follow-up scans should be appropriate in case the affliction with the medical condition is indicated. Furthermore, the lookup tables can contain the respective diagnostic goals that should be pursued by the follow-up scan.

In case the follow-up scan is to be performed using the same medical imaging modality that was already used for the first scan, the decision engine may e.g. base its decisions on such medical conditions, which can be appropriately diagnosed using exactly this imaging modality (i.e. in this case the lookup tables should be restricted to the respective diagnostic goals that can be achieved using exactly this imaging modality).

In case the input data (i.e. the clinical findings) comprise a more complex structure, e.g. a set of numerical values or the above-described spatially-resolved localization data, the decision engine may e.g. employ more sophisticated processing means, e.g. the processing of the clinical findings to generate the decision can employ a trained (deep) neural network.

The disclosure may be considered independent from the architecture of the decision engine. In the decision module, a decision engine may be implemented, wherein its output is modified according to the disclosure or a specially trained and/or structured decision engine could be used, wherein the training was specially drawn to produce the desired output. A n example decision engine may comprise ML-networks for the inputs (clinical findings and e.g. additional patient data) and comprise a plurality of fully connected layers to combine the outputs of the ML-networks to produce decision data.

An example (deep) neural network can have the clinical findings assigned to respective input nodes and the decision assigned to respective output nodes. In case the clinical findings comprise (a set of) numerical values, the number of input nodes of the neural network can correspond to the number of numerical values, and each of the input nodes can be assigned one of the numerical values. In case the clinical findings comprise spatially-resolved localization data (i.e. the clinical findings can be regarded as image data), the spatially-resolved localization data can be fed into a corresponding number of input nodes of the neural network.

In an embodiment, the neural network produces the decision at its respective output node(s) as follows:

- in case the decision is embodied as a binary decision, whether a follow-up scan is needed or advantageous based on the clinical findings, the binary decision can be presented at a single binary output node of the neural network;
- in case the decision comprises a selection of a specific follow-up scan that is needed or advantageous based on the clinical finding, the corresponding selection can be presented at one or multiple output nodes of the neural network; and
- in case the decision comprises an indication, what kind of diagnostic goal should be pursued by the follow-up scan, i.e. which medical condition, which is suspected based on the clinical findings, should be the target of the follow-up scan, the output nodes of the neural network can have a more complex structure.

Generating data in which the decision engine classifier can originate its work may be implemented e.g. on two types of training. Both types described in the following can also be combined.

The first example for training of the decision engine classifier, e.g. the training of the neural network is based on an analysis of previously-performed imaging studies (with a follow-up scan performed and without a follow-up scan performed). Additionally, the parameters of the follow-up scan can be used (indicating what kind of diagnostic goal was pursued by the follow-up scan), and data related to the first scan and the follow-up scan can be reported. In this case, imaging studies comprising a follow-up scan may e.g. correspond to training data of a first category (i.e. "follow-up scan needed") and imaging studies not comprising a follow-up scan correspond to training data of a second category (i.e. "no follow-up scan needed"). Based on the training data in the first category and the second category, the classifier contained by the decision engine, e.g. the neural network, can be trained. Such training data can be generated based on a monitoring of the performance of several imaging studies on different medical imaging machines, e.g. employing the "Virtual Cockpit" technology. Such data can be transferred from the medical imaging machines via a network to the severs of the providers of the embodiments of the method as discussed herein. Therefore, it is possible that also rare and complex diagnostic questions can be assessed by the decision engine based on "human scan coaches," which the decision engine learns from (from a commercial perspective, one can also assess the usage frequency of different use cases to assess which use cases should be automated first). By this method, training data can be generated for the decision engine without having to perform a manual annotation.

The second example possibility to generate data which the decision engine classifier can base its work on the following method: Based on the initial medical imaging data and clinical findings (e.g. of a CAD engine), a location of the patient in a certain clinical pathway is determined. Accordingly, a suitable follow-up scan is determined based on the current location of the patient in the clinical pathway and an analysis of linked nodes in the clinical pathway (e.g. supported by the AI Pathway Companion).

Generally, the output of a decision engine comprises at least an information, e.g. whether a further imaging examination is necessary or not. Instead of a further imaging examination, other types of diagnostic tests (e.g. laboratory tests etc.) can be used. The further imaging examination can be necessary e.g. due to two reasons:

A. the first imaging examination was not able to answer the posed diagnostic question for sure (example: the first imaging examination was an X-ray scan to determine the presence of possible lung nodules, which did not have a result beyond doubt (e.g. not exceeding a threshold probability), so a second imaging examination using a computed tomography apparatus needs to be scheduled); and B. the first imaging examination resulted in an accidental finding (e.g. unrelated to the diagnostic purpose of the first imaging examination) that needs a confirmation or a quantification by another imaging examination.

The main input of the parameter setting engine is the decision data generated by the decision engine. In the case in which the decision indicates that a follow-up scan is necessary or advantageous, the parameter setting engine will generate a second set of values, the suggested set of imaging parameter values, which can then be set for further recording the number of images (e.g. a second scan) with a medical imaging system (a "follow-up scan").

The parameter setting engine can generate the suggested set of imaging parameter values based on the decision data as an input. For instance, if the decision data indicates what kind of diagnostic goal should be pursued by the follow-up scan, i.e. which medical condition (that is suspected based on the clinical findings), should be the target of the follow-up scan. The parameter setting engine can generate suggested set of imaging parameter values, which are suitable for pursuing the specific diagnostic goal indicated by the decision.

In addition, the determined clinical findings (e.g. generated by the CAD engine) and/or the initial set of imaging parameter values can be used as further inputs for the parameter setting engine.

The parameter setting engine can comprise a (e.g. deep) neural network, having the following input nodes:

The input nodes of the neural network can be adapted to the output nodes of the neural network of the decision engine (i.e. the information from the output nodes of the neural network of the decision engine can be passed in a suitable way to the input nodes of the decision engine);

further input nodes can be foreseen for the clinical findings (e.g. generated by the CAD engine) and/or the initial set of imaging parameter values.

The output nodes of the (e.g. deep) neural network can be embodies as follows:

Each output node can be assigned a specific set of imaging parameters, which is particularly suitable for performing a scan directed to a specific diagnostic goal. In this case, the result of the processing by the neural network can indicate, which specific set of imaging parameters is chosen for the follow-up scan.

Additionally or alternatively, each output node can be assigned a specific imaging parameter. The value of the output node can then be set for the specific imaging parameter when performing the follow-up scan. In this case, the number of output nodes can correspond to the number of imaging parameters to be set for the follow-up scan.

The training of the parameter setting engine may be performed similar to the training of the decision engine; the training of the parameter setting engine can be performed based on an analysis of previously performed imaging studies. In case of the parameter setting engine, it makes sense to take only imaging studies into consideration, in which a follow-up scan has been performed.

Examples of suitable training data to be gathered could comprise the following information solely or in combination:

an initial set of imaging parameter values used in the imaging studies used for training;

clinical findings found in the imaging studies used for training;

a diagnostic goal to be pursued in the follow-up scan of the imaging studies used for training; and a suggested set of imaging parameter values set for a follow-up scan in the imaging studies used for training.

Again, such training data can be generated based on a monitoring of the performance of several imaging studies on different medical imaging machines, e.g. employing the "Virtual Cockpit" technology (see corresponding paragraph regarding the decision engine). Again, the location of the patient in a certain clinical pathway can be considered.

The parameter setting engine and the decision setting engine may be embodied separately from another (e.g. as separate neural networks) or formed as a combined engine (e.g. as one single neural network). For example, the decision engine may comprise a neural network for generating decision data from clinical findings, and the parameter setting engine may be a following neural network for generating a suggested set of imaging parameter values from the decision data. In another example, a single neuronal network may be implemented for generating decision data and the suggested set of imaging parameter values.

Concerning the example of the separate implementation of the decision engine and the parameter setting engine, the parameter setting engine mat take the outputs of the decision engine as inputs and process them to generate the suggested set of imaging parameter values. Concerning the example of the combined implementation of the decision engine and the parameter setting engine, a combined engine (including the functionality of the decision engine and the parameter setting engine) may be implemented.

The combined engine takes the clinical findings as an input and processes them to generate the suggested set of imaging parameter values. Optionally, the combined engine can take the initial set of imaging parameter values as an input, also.

An advantageous implementation of the combined engine is an embodiment as a "multitask network." Such neural network can solve multiple tasks, i.e. the generation of the decision if a follow-up scan should be performed and the setting of the suggested set of imaging parameter values for the follow-up scan. In an embodiment, information is shared across the multiple tasks of the multitask network, i.e. the decision generated by the multitask network can influence the setting of the suggested set of imaging parameter values. For example, all tasks of the multitask network may be trained simultaneously using a suitable set of training data (see training data for decision engine and parameter setting engine). A preferred multitask network typically has task-specific layers dedicated for generating the decision, and task-specific layers dedicated for generating the suggested set of imaging parameter values (e.g. the output layers of the multitask network). An example multitask network typically has shared (e.g. hidden) layers between both tasks. Such a multitask network allows an efficient processing and training of the tasks required for the test-algorithm chain in diagnostic imaging.

The decision data and the suggested set of imaging parameter values are then outputted.

This may result in a further imaging examination of the patient. One advantage of this procedure is that decision data may be present very fast. Thus, in the case the decision data indicates that the modality for the first and the second imaging examination could be the same, the further imaging examination can be executed directly after the first imaging examination (e.g. subsequent to a first scan). For example, the further imaging examination can be defined by another protocol sequence to be executed during or after a predefined protocol sequence, e.g. due to diagnostic uncertainty or due to incidental findings. In the case in which the same modality is used, there is no need to explicitly output decision data. The decision data would be the output of the suggested imaging parameter values for this modality.

Thus, the data may e.g. be outputted for recording a number of images of the patient. This recording may also be part of the method according to the disclosure. For instance, this recording may be performed in the course of a scan of a patient (e.g. a "follow-up scan").

Based on the received suggested set of imaging parameter values, the further recording of a number of images of the patient (e.g. a second scan) with a medical imaging system should be performed, at least when the decision data suggest this step. In the case in which the decision data implies that there is no need for this step, then e.g. there is also no suggested set of imaging parameter values produced (since there is no scan suggested).

The second scan with the medical imaging system produces further medical imaging data, which should differ from the initial medical imaging data (e.g. in contrast, resolution, spatial coverage, etc.), since otherwise all further examinations could have been made with the initial imaging data. It is advantageous that the second medical imaging data should be useful for pursuing the specific diagnostic goal which was prescribed by the decision data based on the clinical findings (e.g. generated by the CAD engine). Thus, the suggested set of imaging parameter values should be rendered such that the follow-up scan is specially adapted for an examination concerning the clinical finding.

In an embodiment, the medical imaging system used for the second scan is the same medical imaging system that was used for the first scan. In this scan, the follow-up scan of the patient can be performed in the same medical imaging system, which excludes the need for repositioning the patient.

In an embodiment, the follow-up scan is performed immediately after the first scan is performed, without repositioning of the patient. In this case, the automatic processing of the initial medical imaging data (by the CAD engine, decision engine and parameter setting engine) leads to immediately performing the second scan (without the necessity that the initial medical imaging data are assessed by a radiologist).

Of course, it is also possible to extend the ideas presented in this disclosure to multi-modality imaging. In this case, the follow-up scan using a different imaging modality can be scheduled immediately so that the patient does not have to leave the hospital facilities before the follow-up scan is performed.

Typically, the performance of the follow-up scan is ordered by an authorized person before it is started (e.g. when the follow-up scan includes the application of x-ray dose to the patient). Therefore, the initial medical imaging data, the output of the CAD engine, the output of the decision engine, and/or the output of the parameter setting engine may be e.g. presented to the authorized person. The authorized person can then confirm that the follow-up scan should be performed based on the suggested set of imaging parameter values generated by the parameter setting engine. An example implementation of such a method is possible using a "confirmation UI," which is implemented similarly as described in U.S. patent application Ser. No. 17/012,136 for the AI Rad Companion results.

As indicated above, the method according to the disclosure may also derive results by using additional information. In one example, this may include the use of patient attributes and/or sensor data of the patient.

A control device according to the disclosure for controlling a medical imaging system comprises a clinical decision system according to the disclosure. Alternatively or additionally, the control device and/or the clinical decision system is configured to perform the method according to the disclosure. The control device may comprise additional units or devices for controlling components of a medical imaging system.

A medical imaging system according to the disclosure for recording images of a patient in the form of imaging data comprises a decision module according to the disclosure, and a clinical decision system according to the disclosure. In an embodiment, the medical imaging system comprises a control device according to the disclosure. The medical imaging system may be configured for magnetic resonance imaging (MRI), computed tomography (CT), X-ray imaging, positron emission tomography (PET), single-photon emission computed tomography (SPECT), ultrasound, molecular imaging, or any other suitable medical imaging procedures.

Some units or modules of the disclosure mentioned above can be completely or partially realized as software modules (e.g. computer-readable and/or executable instructions) running on and/or being configured to be executed by a processor of a computing system (e.g. a control device). A realization largely in the form of software can have the advantage that applications already installed on an existing system can be updated, with relatively little effort, to install and run these units of the present application. The object of the disclosure is also achieved by a computer program product with a computer program that is directly loadable into the memory of a computing system, and which comprises program units to perform the steps of the inventive method when the program is executed by the computing system. In addition to the computer program, such a computer program product can also comprise further parts such as documentation and/or additional components, also hardware components such as a hardware key (dongle etc.) to facilitate access to the software.

A computer readable medium such as a memory stick, a hard-disk or other transportable or permanently-installed carrier can serve to transport and/or to store the executable parts of the computer program product so that these can be read from a processor unit of a computing system. A processor unit can comprise one or more microprocessors or processing circuitry, or their equivalents.

Particularly advantageous embodiments and features of the disclosure are described herein, including the claims, as revealed in the following description. Features of different claim categories may be combined as appropriate to give further embodiments not described herein.

According to a preferred method, in the course of providing images, an initial set of imaging parameter values is provided, e.g. by a semi-automatic or automatic process, and an image is recorded based on the initial set of imaging parameter values and the resulting initial imaging data is provided for the determination of findings and e.g. also for the generation of the suggested set of imaging parameter values. Since the method according to the disclosure could produce results fast, further images of the patient could be recorded when needed (when the decision data indicates this) with the same modality. Concerning an MRI system, the two imaging procedures may occur so fast behind each other that the patient does not recognize that there have been made two examinations.

Typically, before the setting of the initial set of imaging parameter values, patient attributes are gathered, e.g. in the process of the patient registration. Patient attributes may e.g. comprise information of the group of medical history of patient, population-specific data (e.g. age, gender, etc.) and patient-specific parameters (e.g. height, weight, etc.). The patient attributes may e.g. be used as input for the setting of the initial set of imaging parameter values, the determination of clinical findings (e.g. the CAD engine), the generation of decision data (e.g. the decision engine), and/or the suggested set of imaging parameter values (e.g. the parameter setting engine).

During the whole workflow (or during parts of the workflow), sensor data of the patient can be acquired. Such sensor data may e.g. comprise information of the group of optical sensor data (e.g. acquired using a 3D camera), physiological sensor data (e.g. ECG data, blood pressure, etc.) and motion data (e.g. regarding heart and/or breathing motion). The sensor data may e.g. be used as input for the setting of the initial set of imaging parameter values, the performance of the first scan with the medical imaging system, the suggested set of imaging parameter values (e.g. the parameter setting engine), and/or the performance of the second scan with the medical imaging system. The sensor data can be registered with the initial medical imaging data acquired in the first scan and/or the clinical findings (in case the clinical findings comprise localization data). The registered sensor data can then be used for the parameter setting engine to make the second scan more time efficient and/or allow accurate targeting of the second scan (e.g. accurate setting of the field-of-view for the second scan) and/or make the second scan more dose efficient (regarding x-ray dose).

Thus, in an embodiment the initial set of imaging parameter values is based on patient attributes and/or sensor data of the patient and/or findings are determined also based on patient attributes.

Also, the suggested set of imaging parameter values may be based on the generated decision data or generated in the course of generating the decision data. As a further example, the suggested set of imaging parameter values may be based on patient attributes and/or an initial set of imaging parameter values, and/or the clinical findings, and/or sensor data of the patient.

Also, the decision data may e.g. be generated based on patient attributes and/or the initial set of imaging parameter values and/or position-data defining an actual position of the patient in a pathway of a clinical guideline.

Regarding the clinical guideline, the decision module may be configured to generate a decision based on the location of the patient in the pathway of a clinical guideline, wherein the location is given by "position-data." It should be noted that both should be known, i.e. the clinical guideline (at least the steps following from the location of the patient) and the location of the patient in this clinical guideline. This could be realized in that the decision module has access to data comprising information about the complete clinical guideline, in adding the relevant information to the position-data or in training a decision engine on the complete clinical guideline and (all) possible locations of the patient.

Concerning the decision module, the decision module may be implemented as a decision engine that is trained to process a position in a clinical guideline. The decision module may also comprise several decision engines that have been trained for producing decision data for a number of special nodes of a clinical guideline, and the decision module comprises a selection module that is designed to choose the matching decision engine for the node associated with where the patient is located. The decision module may also comprise one e.g. conventional decision engine and a guideline module configured to generate decision data by selecting the output data of the decision engine depending on the position-data and the next steps of the clinical guideline from the actual position of the patient.

A "clinical guideline" or "clinical pathway" may comprise a directed graph comprising nodes and a number of possible following steps (possible treatment recommendations) at each node. A standard-operating procedure is a preferred clinical guideline. As said above, the disclosure does not necessarily need a complete clinical guideline, but at least a directed graph representing at least a part of a medical guideline comprising the node where the patient is located. Concerning a clinical guideline, document EP 3837693 A1 or https://www.nccih.nih.gov/health/providers/clinicalpractice render additional information.

Locating patients in clinical guidelines, as well as creating standard operating procedures based on deviations from guidelines, is generally known, and is e.g. described in EP 3637424 A1.

Thus, the minimum information needed in accordance with the embodiments of the disclosure is the location of the patient (given in the position data) and a number of possible next steps for the patient based on the position of the patient, wherein this number should be greater than one to have the need for a decision. at least one of the possible next steps should refer to a further imaging examination or another type of diagnostic tests e.g. a laboratory test.

The decision data then comprises a number of these next steps as information. This number could be one in the case that only one possibility is desired as output. However, the number could also be larger in the case where there is a plurality of next steps, and individual decision scores for these steps are preferred in the information. Thus, the decision module provides information indicating which next steps from a set of possible next steps of the clinical guideline originating from the actual position of the patient should be performed.

As already said above, the decision data could be generated by the decision module in different ways, e.g.:
- by using a specially trained decision engine;
- by using a (possibly known) decision engine and a guideline module; or
- by using several (possibly known) decision engines and a selection module.

These possibilities may also be combined. For example, may the selection module select (depending on the position data) whether the trained decision engine should be used or the output data should be post processed by the guideline module.

According to an embodiment, after outputting the suggested set of imaging parameter values, a number of images of the patient is recorded, e.g. also based on sensor data of the patient. As an example, further decision data may be generated based on imaging data of the recorded images by performing the steps of the method again, while regarding this imaging data as new initial imaging data. Thus, the method could be performed several times each time after recording a further image.

According to an exemplary clinical decision system, the data interface is configured to receive data comprising patient attributes, and the CAD engine and/or the decision module is configured for producing results based on the patient attributes. In an embodiment, the decision module comprises a decision engine and may also comprise a parameter setting engine, wherein at least one of these engines is configured to produce results based on the patient attributes.

According to a preferred clinical decision system, the data interface is configured to receive sensor data of a patient and wherein the decision module, e.g. a parameter setting engine, is configured to produce results based on the sensor data.

According to an exemplary decision module, the decision module is configured to generate decision information by using a decision engine that has been trained on determined findings, and e.g. also trained on parameter settings used for recording the first medical images and/or attribute-data of the patient (i.e. patient attributes), to generate decision information as output data, wherein the output data also comprises the suggested set of imaging parameter values. Alternatively or additionally, the output data also comprises information about what kind of diagnostic goal should be pursued by a follow-up scan, e.g. which medical condition, which is suspected based on the clinical findings, should be the target of the follow-up scan.

An exemplary decision module comprises a (scan) parameter setting engine configured to generate the imaging parameters based on the output data of the decision engine and e.g. also based on the determined findings and/or parameter settings used for recording the first medical images and/or patient attributes and/or sensor data of the patient.

An exemplary decision module comprises a neural network configured such that the clinical findings are assigned to respective input nodes, and the decision data assigned to respective output nodes. The clinical findings comprise numerical values, and the number of input nodes of the neural network may e.g. correspond to the number of numerical values, and each of the input nodes may e.g. be assigned one of the numerical values. Alternatively or additionally, the clinical findings comprise spatially-resolved localization data, and the spatially-resolved localization data may e.g. be fed into a corresponding number of input nodes of the neural network. In an embodiment, the spatially-resolved localization data comprises a plurality of voxels, and the number of input nodes correspond to the number of voxels.

An exemplary decision module comprises a neural network, e.g. in a decision engine and/or a parameter setting engine. The neural network may be a trained network. It neural network may be trained on training data generated based on a monitoring of a performance of several imaging studies on different medical imaging machines. For instance, the training may be based on an analysis of previously-performed imaging studies, and additionally on the parameters of follow-up scans and data related to the respective first scan and the follow-up scan.

An exemplary decision module comprises a decision engine and a parameter setting engine, each comprising an individual neural network. The input nodes of the neural network of the parameter setting engine are adapted to the output nodes of the neural network of the decision engine. For instance, each output node of the neural network of the parameter setting engine may be assigned a plurality of specific suggested set of imaging parameter values, which is particularly suitable for performing a recording of images directed to a specific diagnostic goal. Alternatively or additionally, each output node of the neural network of the parameter setting engine may be assigned a single specific suggested set of imaging parameter values.

An exemplary decision module comprises a decision engine and a parameter setting engine, wherein the decision engine and the parameter setting engine are combined as a single neural network, and wherein parameters at the input nodes of the single neural network are the clinical findings and parameters at the output nodes of the single neural network comprise the suggested set of imaging parameter values.

In an embodiment, the single neural network (the combined decision engine and parameter setting engine) is designed as a multitask network, e.g. configured for generating the decision data and the setting of the suggested set of imaging parameter values for the follow-up scan.

In an embodiment, information is shared across the multiple tasks of the multitask network, wherein the multitask network has task-specific layers dedicated for generating the decision data and task-specific layers dedicated for generating the suggested set of imaging parameter values.

In an embodiment, components are part of a data-network, wherein e.g. the data-network and a medical imaging system (i.e. the magnetic resonance imaging system which provides image data) are in data communication with each other, wherein the data-network comprises parts of the internet and/or a cloud-based computing system, and wherein e.g. a number of components of the disclosure is realized in this cloud-based computing system. For example, the components of the system may be part of a data-network, wherein the data-network and a medical imaging system which provides the image data are in communication with each other. Such a networked solution may be implemented via an internet platform and/or in a cloud-based computing system.

The method may also include elements of "cloud computing." In the technical field of cloud computing, an IT infrastructure is provided over a data-network, e.g. a storage space or processing power and/or application software. The communication between the user and the "cloud" is achieved by means of data interfaces and/or data transmission protocols.

In the context of cloud computing, in a preferred embodiment of the method according to the disclosure, provision of data via a data channel (for example a data-network) to a cloud takes place. This cloud includes a (remote) computing system, e.g. a computer cluster that typically does not include the user's local machine. This cloud can be made available e.g. by the medical facility, which also provides the medical imaging systems. As an example, the image acquisition data is transmitted to a (remote) computer system (i.e. the cloud) via a RIS (Radiology Information System), via a PACS (Picture Archiving and Communication System), etc.

Within the scope of an embodiment of the disclosure, the abovementioned components (e.g. the "engines") may all or partly present on the cloud side. For instance, an embodiment further comprises a local computing unit connected to the system via a data channel (e.g. a data-network, e.g. configured as RIS or PACS). The local computing unit includes at least one data receiving interface to receive data. Moreover, the local computer may e.g. additionally have a transmission interface to send data to the system.

This disclosure provides a useful dedicated implementation of a test-algorithm chain in medical imaging and lists corresponding implementation details. The described implementation enables a (semi)automatic prescription of a follow-up medical scan of a patient, allowing that the follow-up medical scan is performed immediately after the first scan. Furthermore, the follow-up medical scan is advantageously adapted to the clinical findings revealed by the first scan.

BRIEF DESCRIPTION OF THE DRAWINGS/FIGURES

Other objects and features of the present disclosure will become apparent from the following detailed descriptions considered in conjunction with the accompanying drawings. It is to be understood, however, that the drawings are designed solely for the purposes of illustration and not as a definition of the limits of the disclosure.

In the diagrams, like numbers refer to like objects throughout. Objects in the diagrams are not necessarily drawn to scale.

DETAILED DESCRIPTION

Figure 1:
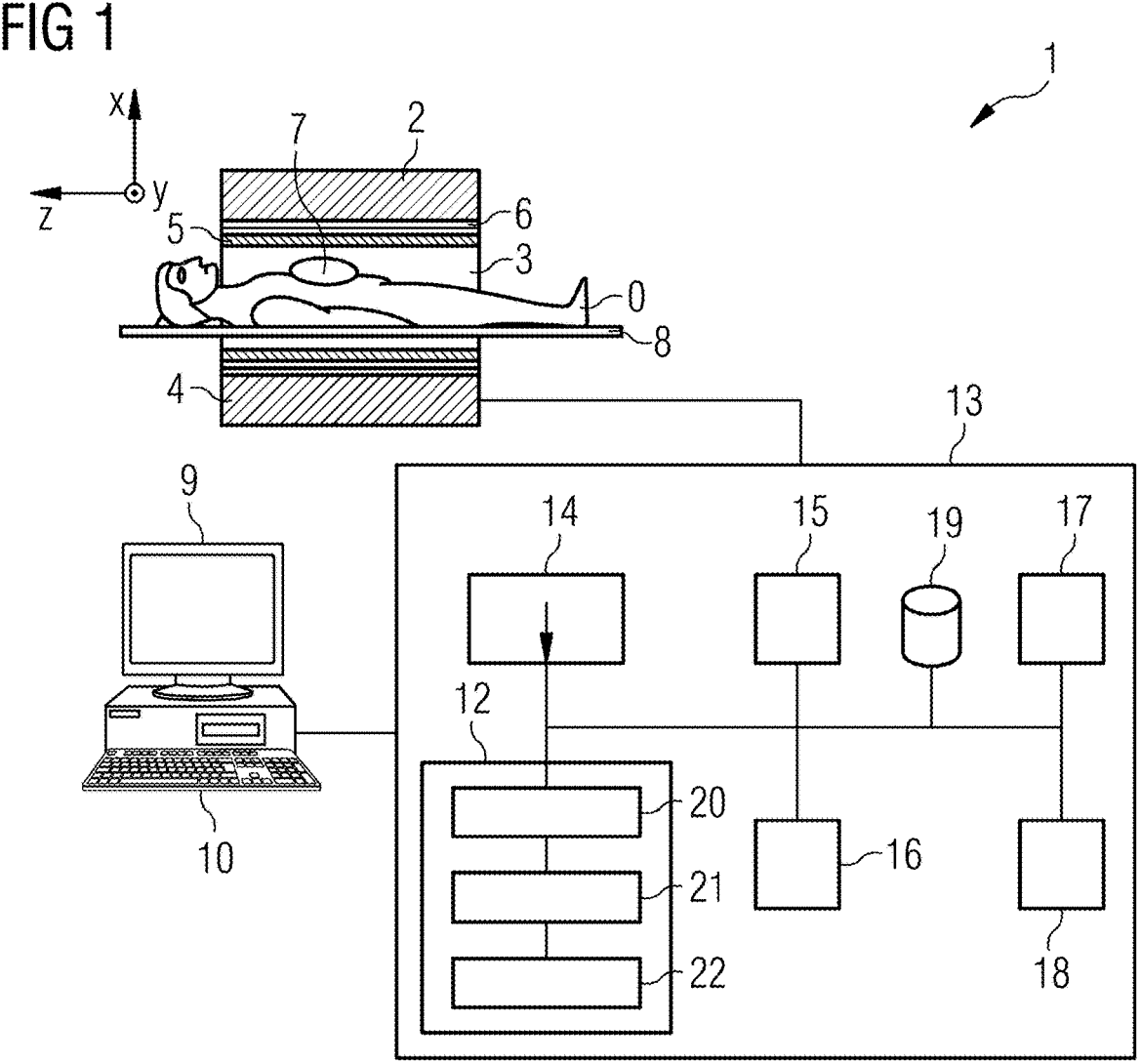
FIG. 1 shows a simplified MRI system according to an embodiment of the disclosure.

FIG. 1 shows a schematic representation of a magnetic resonance imaging system 1 (e.g. an "MRI-system") as an example for a medical imaging system. The MRI system 1 includes the actual magnetic resonance scanner (data acquisition unit) 2 with an examination space 3 or patient tunnel in which a patient or test person is positioned on a driven bed 8, in whose body the actual examination object is located.

The magnetic resonance scanner 2 is typically equipped with a basic field magnet system 4, a gradient system 6, as well as an RF transmission antenna system 5 and an RF reception antenna system 7. In the shown exemplary embodiment, the RF transmission antenna system 5 is a whole-body coil permanently installed in the magnetic resonance scanner 2, in contrast to which the RF reception antenna system 7 is formed as local coils (symbolized here by only a single local coil) to be arranged on the patient or test subject. In principle, however, the whole-body coil can also be used as an RF reception antenna system, and the local coils can respectively be switched into different operating modes.

The basic field magnet system 4 is configured such that images can be recorded. The basic field magnet system 4 is configured in a typical manner so that it generates a basic magnetic field in the longitudinal direction of the patient, i.e. along the longitudinal axis of the magnetic resonance scanner 2 that proceeds in the z-direction. The gradient system 6 typically includes individually controllable gradient coils to be able to switch (activate) gradients in the x-direction, y-direction, or z-direction independently of one another.

The MRI system 1 shown here is a whole-body system with a patient tunnel into which a patient can be completely introduced. However, in principle the disclosure can also be used at other MRI systems, for example with a laterally open, C-shaped housing, as well as in smaller magnetic resonance scanners in which only one body part can be positioned.

Furthermore, the MRI system 1 has a central control device 13 that is used to control the MRI system 1. This central control device 13 includes a sequence control unit 14 for measurement sequence control. With this sequence control unit 14, the series of radio-frequency pulses (RF pulses) and gradient pulses can be controlled depending on a selected pulse sequence within a measurement session. For example, such a series of pulse sequence can be predetermined within a measurement or control protocol. Different control protocols for different measurements or measurement sessions are typically stored in a memory 19 and can be selected by and operator (and possibly modified as necessary) and then be used to implement the measurement.

To output the individual RF pulses of a pulse sequence, the central control device 13 has a radio-frequency transmission device 15 that generates and amplifies the RF pulses and feeds them into the RF transmission antenna system 5 via a suitable interface (not shown in detail). To control the gradient coils of the gradient system 6, the control device 13 has a gradient system interface 16. The sequence control unit 14 communicates in a suitable manner with the radio-frequency transmission device 15 and the gradient system interface 16 to emit the pulse sequence.

Moreover, the control device 13 has a radio-frequency reception device 17 (likewise communicating with the sequence control unit 14 in a suitable manner) to acquire magnetic resonance signals (i.e. raw data) for the individual measurements, which magnetic resonance signals are received in a coordinated manner from the RF reception antenna system 7 within the scope of the pulse sequence.

A reconstruction unit 18 receives the acquired raw data and reconstructs magnetic resonance image data therefrom for the measurements. This reconstruction is typically performed on the basis of parameters that may be specified in the respective measurement or control protocol. For example, the image data can then be stored in a memory 19.

Operation of the central control device 13 can take place via a terminal 10 with an input unit and a display unit 9, via which the entire MRI system 1 can thus also be operated by an operator. MR images can also be displayed at the display unit 9, and measurements can be planned and started by means of the input unit (possibly in combination with the display unit 9), and e.g. suitable control protocols can be selected (and possibly modified) with suitable series of pulse sequence as explained above.

The control device 13 comprises a clinical decision system 12 configured to perform the method according to the disclosure. This clinical decision system 12 comprises the following components that are referred to herein as modules or software modules (see also the following figures describing the function of the components). These modules may thus be implemented as software (e.g. instructions executable via a processor, processing circuitry, etc.), as hardware dedicated components (e.g. an application specific integrated circuit (ASIC), a field programmable gate array (FPGA), etc., or combinations of software and hardware components, in various embodiments.

A data interface 20 is configured to receive initial imaging data D1 from a preceding examination of a patient, and position-data PD defining a position of the patient in a pathway of a predefined clinical guideline G, and in this example also for outputting the decision data DD.

A CAD engine 21 is configured to determine clinical findings F by automated processing of the initial imaging data D1.

A decision module 22 is configured to generate decision data DD based on the determined findings F, the position data PD, and the structure of the clinical guideline G.

The MRI system 1 according to the disclosure, and e.g. the control device 13, may have any suitable number of additional components that are not shown in detail, but are typically present at such systems, for example a network interface to connect the entire system with a network and be able to exchange raw data and/or image data or, respectively, parameter maps, but also additional data (for example patient-relevant data or control protocols).

The manner by which suitable raw data are acquired by radiation of RF pulses and the generation of gradient fields, and MR images are reconstructed from the raw data, is generally known to those skilled in the art, and thus need not be explained in detail herein.

Figure 2:
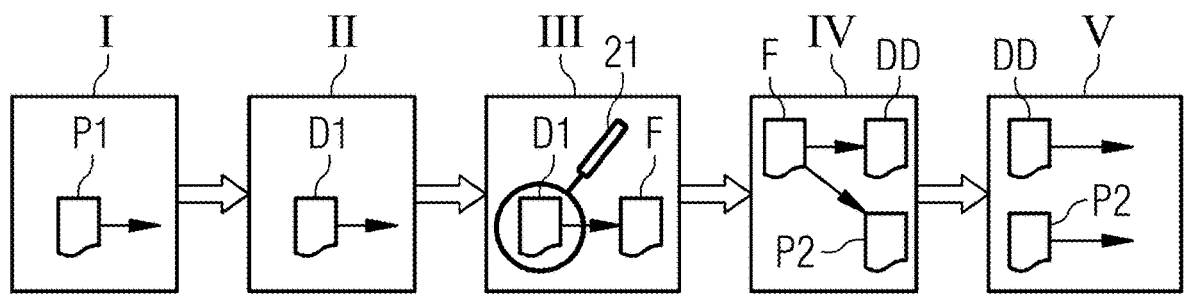
FIG. 2 shows a block diagram of the process flow of a method according to an embodiment of the disclosure.

FIG. 2 shows a block diagram of the process flow of a preferred method according to an embodiment of the disclosure for image-based operational decision support.

In step I, an initial set of imaging parameter values P1 is provided, e.g. by a semi-automatic or automatic process.

In step II, an image is recorded based on the initial set of imaging parameter values P1 and the resulting initial imaging data D1 is provided for the next steps of the method.

In step III, clinical findings F are determined by automated processing of the initial imaging data D1.

In step IV, decision data DD is generated at least comprising a decision whether a further recording of a number of images is necessary. In addition, a suggested set of imaging parameter values P2 is generated for recording this number of images, wherein the decision data DD is based on the determined clinical findings F.

In step V, the suggested set of imaging parameter values P2 for recording a number of images of the patient and here also the decision data DD is outputted.

Figure 3:
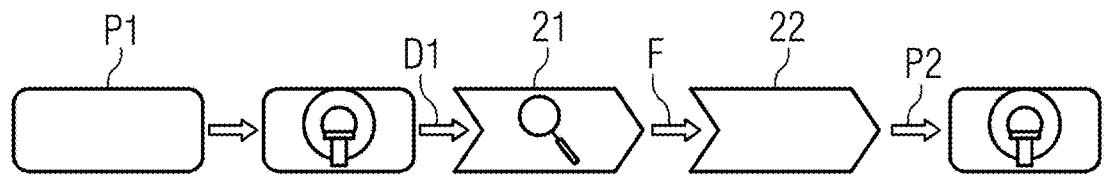
FIG. 3 shows an example of a test-algorithm chain according to an embodiment of the disclosure.

FIG. 3 shows an example of a test-algorithm chain according to an embodiment of the disclosure. From left to right, an initial set of imaging parameter values P1 is provided for a first scan procedure (symbolized by an MRI scanner) producing an initial set of imaging data D1. This initial imaging data D1 is then examined for findings F by a CAD engine 21 that are further used by a decision module 22 to produce a suggested set of imaging parameter values P2 for a following scan procedure (right box).

Here and in the following figures, the arrow-shaped boxes could be regarded to represent the clinical decision system (with additional data interfaces for inputs and outputs).

Figure 4:
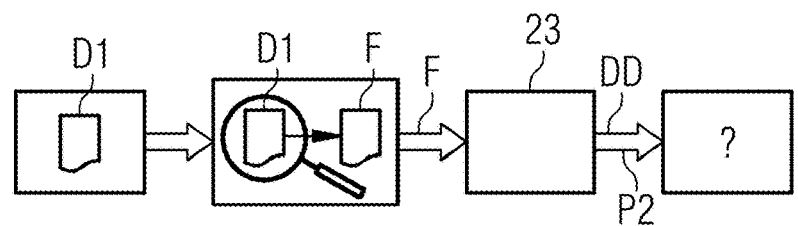
FIG. 4 shows an embodiment of the disclosure with a trained decision engine.

FIG. 4 shows an embodiment of the disclosure with a trained decision engine 23. Here, the findings F, and optionally also additional patient data (not shown), are inputted in the decision engine 23. The decision engine 23 then generates decision data DD based on the input data and a suggested set of imaging parameter values P2.

Figure 5:
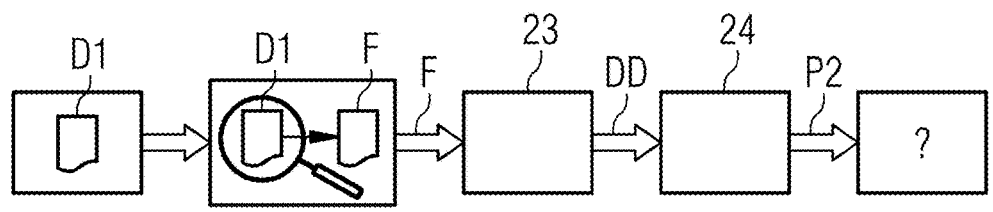
FIG. 5 shows an embodiment of the disclosure with a decision engine and a parameter setting engine.

FIG. 5 shows an embodiment of the disclosure with a decision engine 23 and a parameter setting engine 24. In contrast to FIG. 4, this embodiment does not need a trained decision engine 23. The suggested set of imaging parameter values P2 is generated based on the decision data DD and outputted. The decision data DD could also be outputted.

Figure 6:
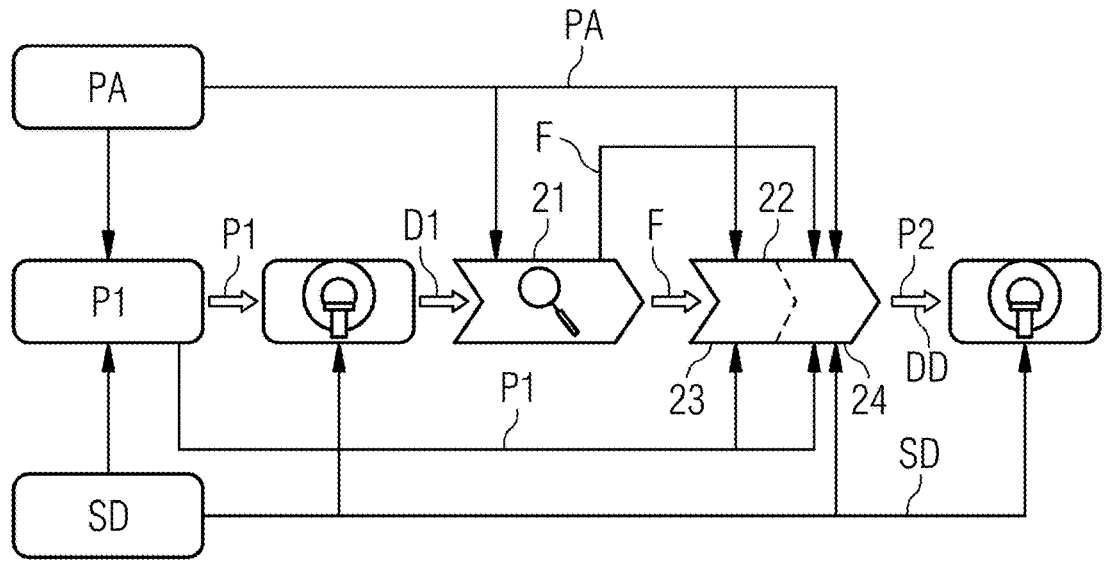
FIG. 6 shows another example of a test-algorithm chain according to an embodiment of the disclosure.

FIG. 6 shows a further example of a test-algorithm chain according to an embodiment of the disclosure. The main chain is similar to FIG. 3, but in contrast to FIG. 3, there are shown further possible data-streams and the decision module 22 is here a combination of a decision engine 23 and a parameter setting engine 24. In this example, the initial set of imaging parameter values P1 is not only used for the first imaging examination, but also for the decision module 22 (here the decision engine 23 and/or the parameter setting engine 24). Findings F of the CAD engine 21 may also be used by the parameter setting engine 24. Patient attributes PA (i.e. attribute data of a patient) may be used to generate the initial set of imaging parameter values P1, used by the CAD engine 21, used by the decision engine 23 and used by the parameter setting engine 24. Sensor data SD of a patient may be used to generate the initial set of imaging parameter values P1, used for the first and the further imaging examination, and used by the parameter setting engine 24.

Although the present disclosure has been disclosed in the form of preferred embodiments and variations thereon, it will be understood that numerous additional modifications and variations could be made thereto without departing from the scope of the disclosure. For the sake of clarity, it is to be understood that the use of "a" or "an" throughout this application does not exclude a plurality, the expression "a number of" means "at least one", and "comprising" does not exclude other steps or elements. The mention of a "module" or a "system" does not preclude the use of more than one module or device.

The various components described herein may be referred to as "units" or "modules." Such components may be implemented via any suitable combination of hardware and/or software components as applicable and/or known to achieve the intended respective functionality. This may include mechanical and/or electrical components, processors, processing circuitry, or other suitable hardware components configured to execute instructions or computer programs that are stored on a suitable computer readable medium. Regardless of the particular implementation, such devices and units, as applicable and relevant, may alternatively be referred to herein as "circuitry," "processors," or "processing circuitry."

What is claimed is:

1. A method for image-based operational decision support, comprising:
generating initial imaging data from an initial examination of a patient;
determining, via automated processing of the initial imaging data, clinical findings;
generating decision data comprising a decision of whether a further recording of a number of medical images of the patient is required via a subsequent examination of the patient using a respective imaging modality, the decision data being based on the determined clinical findings;
when the decision data indicates that the further recording of the number of images is required, generating a suggested set of imaging parameter values for the further recording of the number of medical images of the patient,
wherein the suggested set of imaging parameter values define a manner in which the subsequent examination is to be performed via the imaging modality based upon the determined clinical findings; and
outputting the suggested set of imaging parameter values for the further recording of the number of images of the patient.

2. The method according to claim 1, wherein in the set of generating the initial imaging data comprises:
generating an initial set of imaging parameter values; and
recording an image based on the initial set of imaging parameter values as part of the initial examination of the patient,
wherein the generating the suggested set of imaging parameter values is based upon the initial imaging data, and
wherein the initial set of imaging parameter values is based on patient attributes and/or sensor data associated with the patient.

3. The method according to claim 1, wherein the generating the decision data comprises:
generating the decision data further based on a position of the patient in a pathway of a clinical guideline.

4. The method according to claim 1, wherein the generating the suggested set of imaging parameter values comprises:
generating the suggested set of imaging parameter values based on the generated decision data and further based on one or more of (i) patient attributes, (ii) an initial set of imaging parameter values, (iii) the clinical findings, or (iv) sensor data associated with the patient.

5. The method according to claim 1, wherein the suggested set of imaging parameter values are identified with a control of an imaging modality for further recording the number of medical images of the patient.

6. The method according to claim 1, wherein the generating the decision data comprises:
generating the decision data via a decision engine that has been trained on one or more of (i) clinical findings, (ii) parameter settings used for recording the initial imaging data, or (iii) patient attributes, to generate the decision data as output data,
wherein the output data further comprises the suggested set of imaging parameter values and/or information about a diagnostic goal of a follow-up scan.

7. The method according to claim 6, wherein the generating the suggested set of imaging parameter values comprises:
generating the suggested set of imaging parameter values based on the decision data output via the decision engine and further based on one or more of (i) the clinical findings, (ii) parameter settings used for recording the initial imaging data, (iii) patient attributes, or (iv) sensor data associated with the patient.

8. The method according to claim 1, wherein:
the clinical findings are assigned to respective input nodes of a neural network,
the decision data is assigned to respective output nodes of the neural network,
the clinical findings comprise numerical values,
a number of input nodes of the neural network correspond to a number of the numerical values, and
each of the input nodes are assigned to one of the numerical values.

9. The method according to claim 1, wherein:
the clinical findings are assigned to respective input nodes of a neural network and the decision data is assigned to respective output nodes of the neural network,
the clinical findings comprise spatially-resolved localization data that is fed into a corresponding number of input nodes of the neural network,
the spatially-resolved localization data comprises a plurality of voxels, and
a number of input nodes correspond to a number of the plurality of voxels.

10. The method according to claim 1, wherein the acts of generating the decision data and the suggested set of imaging parameter values comprise:
training a neural network on training data generated based on a monitoring of a performance of a plurality of imaging studies on different medical imaging machines, and
wherein the training of the neural network is further based on an analysis of previously performed imaging studies, parameters of follow-up scans, and data related to the recording the initial imaging data and a follow-up scan.

11. The method according to claim 1, wherein the acts of generating the decision data and the suggested set of imaging parameter values comprise:
generating the decision data and the suggested set of imaging parameter values via a decision engine and a parameter setting engine, respectively, each of the decision engine and the parameter setting engine comprising a respective individual neural network, and
wherein input nodes of the neural network of the parameter setting engine are adapted to output nodes of the neural network of the decision engine.

12. The method according to claim 11, wherein:
the decision engine and the parameter setting engine are combined as a single neural network,
parameters at the input nodes of the single neural network comprise the clinical findings, and
parameters at the output nodes of the single neural network comprise the suggested set of imaging parameter values.

13. The method according to claim 12, wherein the single neural network is configured as a multitask network, which generates the decision data and the suggested set of imaging parameter values for a follow-up scan.

14. The method according to claim 13, wherein:
information is shared across multiple tasks of the multitask network, and
the multitask network has task-specific layers dedicated for generating the decision data and task-specific layers dedicated for generating the suggested set of imaging parameter values.

15. A system for image-based operational decision support, comprising:
a data interface configured to receive initial imaging data from an initial a preceding examination of a patient; and
processing circuitry configured to:
determine clinical findings by automated processing of the initial imaging data;
generate decision data comprising a decision of whether a further recording of a number of medical images of the patient is required via a subsequent examination of the patient using a respective imaging modality; and
when the decision data indicates that the further recording of the number of images is required, generate a suggested set of imaging parameter values for the further recording of the number of medical images of the patient, the decision data being based on the determined clinical findings,
wherein the suggested set of imaging parameter values define a manner in which the subsequent examination is to be performed via the imaging modality based upon the determined clinical findings, and
wherein the data interface is further configured to output the suggested set of imaging parameter values for the further recording of the number of images of the patient.

16. A non-transitory computer-readable medium configured to store a computer program that, when executed by processing circuitry associated with a control system of a medical imaging system, cause the medical imaging system to:
generate initial imaging data from an initial examination of a patient;
determine, via automated processing of the initial imaging data, clinical findings;
generate decision data comprising a decision of whether a further recording of a number of medical images of the patient is required via a subsequent examination of the patient using a respective imaging modality;
when the decision data indicates that the further recording of the number of images is required, generate a suggested set of imaging parameter values for the further recording of the number of medical images of the patient, the decision data being based on the determined clinical findings,
wherein the suggested set of imaging parameter values define a manner in which the subsequent examination is to be performed via the imaging modality based upon the determined clinical findings; and
outputting the suggested set of imaging parameter values for the further recording of the number of images of the patient.

17. The method according to claim 1, wherein the determined clinical findings comprise a clinical diagnosis and an accompanying probability of the clinical diagnosis.

18. The method according to claim 1, wherein the decision data indicates a target diagnostic goal to be achieved in the subsequent examination of the patient.

19. The method according to claim 1, further comprising:
performing the subsequent examination of the patient after the initial examination of the patient without repositioning the patient between the initial and the subsequent examinations.

20. The method according to claim 1, wherein the initial examination of the patient and the subsequent examination of the patient are performed via the same imaging modality.

* * * * *